United States Patent

Bonnet et al.

[11] Patent Number: 5,969,161
[45] Date of Patent: Oct. 19, 1999

[54] 5-O-DEAOMINYL 6-O-METHYL ERYTHRONOLIDE A DERIVATIVES, METHOD FOR PREPARING SAME AND APPLICATION THEREOF FOR PREPARING BIOLOGICALLY ACTIVE PRODUCTS

[75] Inventors: Alain Bonnet, Chateau Thierry; Michel Delthil, Noisy le Sec; Alain Mazurie, Vaujours, all of France

[73] Assignee: Hoechst Marion Roussel, France

[21] Appl. No.: 09/043,044

[22] PCT Filed: Sep. 10, 1996

[86] PCT No.: PCT/FR96/01384

§ 371 Date: Mar. 10, 1998

§ 102(e) Date: Mar. 10, 1998

[87] PCT Pub. No.: WO97/10251

PCT Pub. Date: Mar. 20, 1997

[30] Foreign Application Priority Data

Sep. 11, 1995 [FR] France ................... 95/10601

[51] Int. Cl.$^6$ .................................................. C07D 313/04
[52] U.S. Cl. ............................................... 549/271
[58] Field of Search ................................ 549/271

[56] References Cited

FOREIGN PATENT DOCUMENTS 272110 6/1988 European Pat. Off. .
619319 10/1994 European Pat. Off. .
619320 10/1994 European Pat. Off. .

*Primary Examiner*—Amelia Owens
*Attorney, Agent, or Firm*—Bierman, Muserlian and Lucas

[57] ABSTRACT

A subject of the invention is the compounds of formula (I):

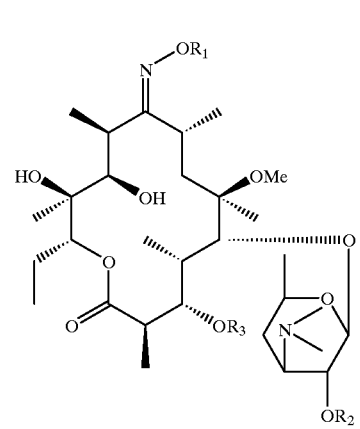

in which $OR_1$, $OR_2$ and $OR_3$ represent hydroxyl radicals blocked in the form of easily cleavable radicals.

The compounds of formula (I) can be used to prepare antibiotic products.

13 Claims, No Drawings

5-O-DEAOMINYL 6-O-METHYL ERYTHRONOLIDE A DERIVATIVES, METHOD FOR PREPARING SAME AND APPLICATION THEREOF FOR PREPARING BIOLOGICALLY ACTIVE PRODUCTS

The present invention relates to new derivatives of 5-O-desosaminyl 6-O-methyl erythronolide A, their preparation process and their use for the preparation of biologically-active products.

A subject of the invention is the compounds of formula (I):

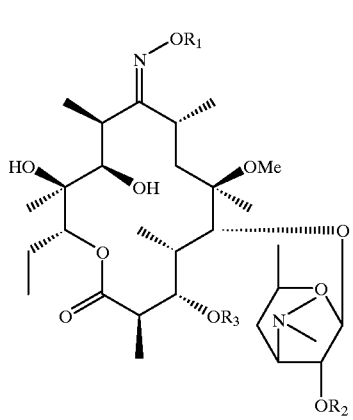

in which:
either $R_1$ represents an alkyl radical containing up to 8 carbon atoms substituted by one or more alkyl radicals containing up to 8 carbon atoms, or by one or more aryl radicals containing up to 14 carbon atoms,
or $R_1$ represents an aryl radical containing up to 14 carbon atoms, optionally substituted by one or more alkyl, alkenyl or alkynyl radicals containing up to 8 carbon atoms, alkoxy or alkylthio radicals containing up to 8 carbon atoms, nitro, $CF_3$ radicals or by one or more halogen atoms,
or $R_1$ represents a radical:

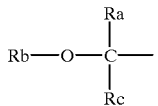

in which Ra represents an alkyl or alkoxy radical containing up to 8 carbon atoms,
Rb represents an alkyl radical containing up to 8 carbon atoms, optionally substituted by a heteroatom,
Rc represents a hydrogen atom or an alkyl radical containing up to 8 carbon atoms,
$R_2$ and $R_3$, identical or different, represent a trialkylsilyl radical in which the alkyl radical contains up to 8 carbon atoms,

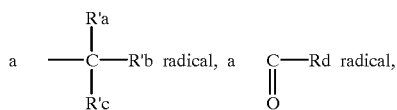

in which R'a, R'b, R'c and Rd represent an alkyl radical containing up to 8 carbon atoms, or an aralkyl radical containing up to 8 carbon atoms, optionally substituted by one or or more of the substituents indicated above for $R_1$.

In the definition of compounds of the invention:
the alkyl, alkenyl or alkynyl radical is preferably one of the following radicals: methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl,
the halogen is preferably fluorine or chlorine, or bromine,
the aryl radical is preferably the phenyl radical, or a naphthyl radical,
the aralkyl radical is preferably a $(C_6H_5)-(CH_2)_a$ radical, a being an integer comprised between 1 and 6, for example the number 1, 2, 3 or 4; the aralkyl radical can be for example, an optionally substituted benzyl radical or a trityl radical,
the alkyloxy radical is preferably one of the following radicals: methoxy, ethoxy, propyloxy isopropyloxy, n-butyloxy, isobutyloxy, tert-butyloxy, n-pentyloxy, isopentyloxy, sec-pentyloxy, tert-pentyloxy, neopentyloxy, n-hexyloxy, sec-hexyloxy, tert-hexyloxy,
the corresponding alkylthio radical can be used by taking the same values and replacing the oxygen atom with a sulphur atom, for example: methylthio, ethylthio. Furthermore, the sulphur atom can be oxidized, for example: methylsulphinyl, methylsulphonyl.

The compounds of the invention can be used for the preparation of compounds of formula (VI):

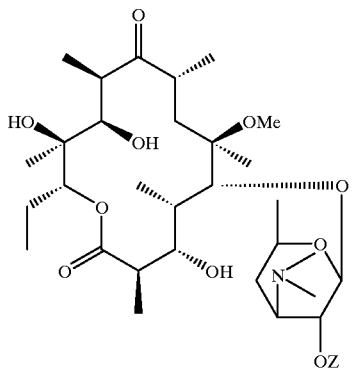

in which Z represents a hydrogen atom or a protective group such as the remainder of a carboxylic acid containing up to 8 carbon atoms, a trialkylsilyl or terbutyl radical. The compounds of formula (VI) are described and claimed in the European Patent Application 0,487,411, as intermediates useful in particular for the preparation of antibiotic products.

A more particular subject of the invention is the compounds of formula (I) in which $R_1$ represents a

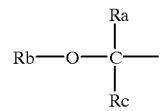

radical in which Ra, Rb and Rc retain the same meaning as previously and in particular those in which Ra, Rb and Rc represent a methyl radical as well as the compounds of formula (I) in which $R_2$ and $R_3$ both represent a trialkylsilyl radical and in particular those in which $R_2$ and $R_3$ represent a trimethylsilyl radical.

A more particular subject of the invention is the compound of formula (I) whose preparation is given hereafter in the experimental part.

A subject of the invention is also a preparation process for the compounds of formula (I) as defined previously, characterized in that the compound of formula (II):

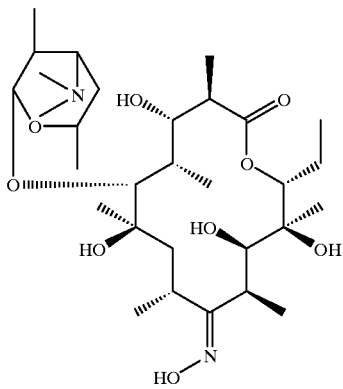

(II)

is subjected to the action of an agent blocking the oxime in position 9, in order to obtain a compound of formula (III):

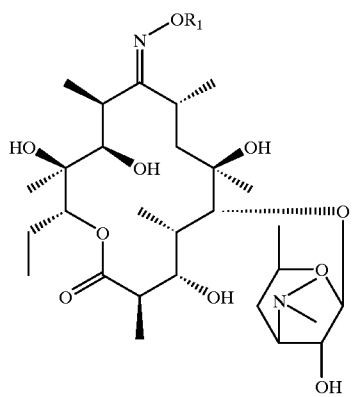

(III)

in which $R_1$ retains its previous meaning, which is subjected to the action of an agent blocking the hydroxyl in position 3 and/or in position 2' in order to obtain the compound of formula (IV):

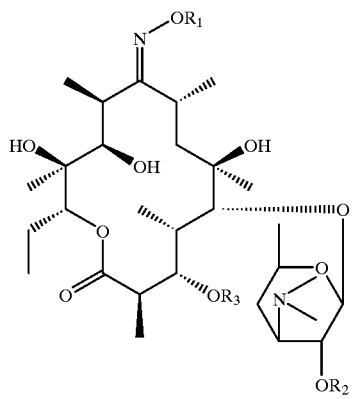

(IV)

in which $R_1$, $R_2$ and $R_3$ retain their previous meaning, which is subjected to the action of a methylation agent of the hydroxyl in position 6, in order to obtain the corresponding compound of formula (I).

The compound of formula (II) used as starting product is a known product described by Le Mahieu et al. in J. Med. Chem. 17 (9) 953–956 (1974).

In a preferred implementation of the process of the invention:

- the oxime in position 9 is protected in the ketal or thioketal form,
- the 3—OH and 2'—OH groups are blocked by trimethylsilyl groups,
- the methylation is carried out using methyl iodide in the presence of a base for example potash, soda, a hydride such as sodium hydride, an alkali metal terbutylate such as for example potassium terbutylate or also in the presence of 1,5-diazabicyclo [4,3,0] non-5-ene or 1,8-diazabicyclo [5,4,0] undec-7-ene.

A subject of the invention is also as new chemical products the products of formula (III) and formula (IV) obtained during the implementation of the process of the invention. A more particular subject of the invention is the products of formulae (III) and (IV) whose preparation is given hereafter in the experimental part.

A subject of the invention is also the use of the compounds of formula (I), characterized in that the compound of formula (I) is subject to the following stages:

- release of the oxime in position 9,
- release of the hydroxyl in position 3 and 2',
- protection of the hydroxyl in position 2'.

A particular subject of the invention is the use characterized in that a compound of formula (I) is subjected to the action of formic acid in the presence of sodium bisulphite or sodium metabisulphite in order to directly obtain the compound of formula (V):

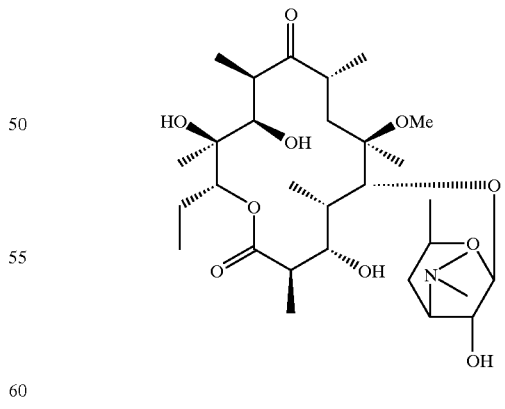

(V)

which is subjected to the action of a protection agent of the hydroxyl in position 2' in order to obtain the compound of formula (VI):

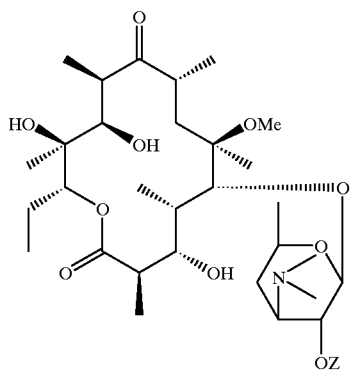

(VI)

in which Z represents a protective group such as the remainder of a carboxylic acid containing up to 8 carbon atoms, or a trialkylsilyl, terbutyl or triphenylmethyl radical.

In addition a subject of the invention is the use characterized in that a compound of formula (I) is subjected to the action of an agent releasing the hydroxyl in position 3 and in position 2' in order to obtain the compound of formula (VII):

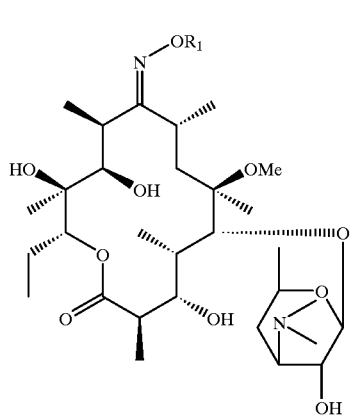

(VII)

in which $R_1$ retains its previous meaning, which is subjected to the action of a protection agent of the OH group in position 2' in order to obtain the compound of formula (VIII):

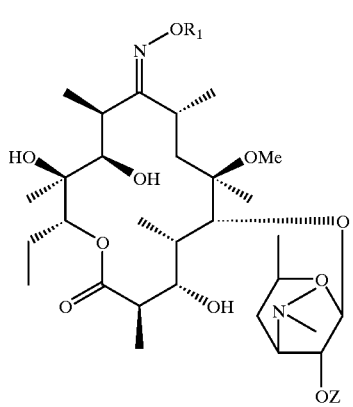

(VIII)

in which $R_1$ retains its previous meaning and Z represents a protective group as defined previously, which is subjected to the action of an agent releasing the 9-oxo group in order to obtain the corresponding compound of formula (VI):

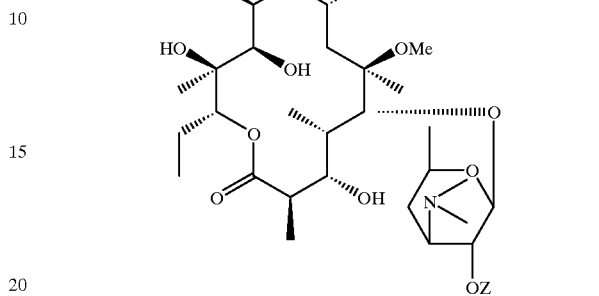

(VI)

in which Z retains its previous meaning.

The following examples illustrate the invention without however limiting it.

EXAMPLE 1

9-O-(1-methoxy-1-methylethyl) oxime of 3-O-de(2, 6-dideoxy-3-C-methyl-3-O-methyl-alpha-L-ribohexopyranosyl)-2',3-O-bis(trimethylsilyl) 6-O-methyl erythromycin.

Stage A:

9-O-(1-methoxy-1-methylethyl) oxime of 3-O-de(2, 6-dideoxy-3-C-methyl-3-O-methyl-alpha-L-ribohexopyranosyl) erythromycin 8.14 g of 9-oxime of 3-O-de(2,6-dideoxy-3-C-methyl-3-O-methyl-alpha-L-ribo-hexopyranosyl) erythromycin, 81.5 ml of methylene chloride, 9.65 ml of 2-methoxy propene and 2.44 g of 98% pyridinium hydrochloride are agitated for half an hour at ambient temperature. 80 ml of a saturated solution of $NaHCO_3$ is added, followed by agitation for 3 minutes. The organic phase is decanted and washed with 50 ml of salt water. The aqueous phases are reextracted with 50 ml of $CH_2Cl_2$. The organic phase is dried over $Na_2SO_4$ and the solvent is evaporated off under reduced pressure. 9 g of desired product is recovered. Yield: 98.5%.

Analytical results:

NMR ($CDCl_3$, 300 MHz)

0.84 (t): $\underline{CH}_3$-$CH_2$; 1.07 (d)-1.09 (d)-1.23 (d)-1.26 (d)x2: the $\underline{CH}_3$-CH's; 2.25 (s): $N(Me)_2$; 2.48 (m): H'$_3$; 2.64 (dq): $H_2$; 2.72 (bq): $H_{10}$; 3.22 (s): OMe; ~3.25: H'$_2$; 3.51 (d): $H_5$; 3.58 (bd): $H_3$; 3.68 (bs): $H_{11}$; ~3.50 (m): H'$_5$; ~3.62 (m): $H_8$ - - - > E; 4.41 (d): H'$_1$; 5.23 (dd): $H_{13}$; 2.36-4.48-3.58: mobile H's.

Stage B:

9-O-(1-methoxy-1-methylethyl) oxime of 3-O-de(2, 6-dideoxy-3-C-methyl-3-O-methyl-alpha-L-ribohexopyranosyl)-2',3-O-bis(trimethylsilyl) erythromycin A mixture of 6.62 g of the product prepared in the preceding stage, 66 ml of $CH_2Cl_2$, 2.95 ml of N-trimethylsilyl imidazole and 1.7 ml of trimethylsilyl chloride is agitated for 45 minutes at ambient temperature. 50 ml of a saturated solution of NaHCO$_3$ is added. The organic phase is decanted and washed with 30 ml of salt water. The aqueous phases are reextracted with 40 ml of CH$_2$Cl$_2$. The organic phase is dried over Na$_2$SO$_4$ and the solvent is evaporated off under reduced pressure. 7.5 g of desired product is recovered. Yield: 92.9%.

Analytical results:

NMR (CDCl$_3$, 300 Mhz)

0.12–0.16 the OTMS's; 0.84 (t): C$\underline{H}_3$-CH$_2$; 1.16 (x2)-1.38-1.45-1.47-1.00-1.25: the C$\underline{H}_3$-CH's; 2.23 (s): N(Me)$_2$; 2.47 (m): H'$_3$; 2.71 (m): H$_2$ and H$_{10}$; 3.16 (dd): H'$_2$; 3.22 (s): OMe; 3.45 (m): H'$_5$; 3.58 (d): H$_5$; 3.66: H$_8$ - - - > E; 3.66 (s): H$_{11}$; 3.98 (bd): H$_3$; 4.2 (dd): H'$_1$; 5.14 (dd): H$_{13}$; 1.90 (s)-3.10-4.44: OH.

Stage C:

9-O-(1-methoxy-1-methylethyl) oxime of 3-O-de(2, 6-dideoxy-3-C-methyl-3-O-methyl-alpha-L-ribo-hexopyranosyl)-2',3-O-bis(trimethylsilyl) 6-O-methyl erythromycin 1.24 g of the product prepared in the preceding stage, 8.7 ml of a dimethyl sulphoxide/tetrahydrofuran mixture 1/1, 190 μl of methyl iodide and 161 mg of 90% powdered potash are agitated for 2 hours at ambient temperature. 10 ml of AcOEt and 10 ml of a 0.5 M monosodium phosphate solution are added. After decanting and reextraction with AcOEt, the organic phase is washed with 5 ml of water, dried over Na$_2$SO$_4$ and the filtrate is concentrated under reduced pressure. 1.2 g of the desired product is obtained. Yield: 95%.

Analytical results:

NMR (CDCl$_3$, 300 MHz)

Possible structure, the SiMe$_3$'s are located at 0.11 and 0.20; 0.84 (t): C$\underline{H}_3$-CH$_2$; 0.95 (d)-0.97 (d)-1.14 (d)-1.17 (d) x 2: the C$\underline{H}_3$-CH's; 1.18-1.35-1.40-1.48 the CH$_3$-CH's; 2.22 (s): N(Me)$_2$; 2.46 (m): H'$_3$; 2.61 (bq): H$_{10}$; 2.72 (dq): H$_2$; 3.01 (s): OMe; 3.13 (dd): H'$_5$; 3.22 (s): OMe chain; 3.45 (m): H'$_5$; ~3.70: H$_8$ - - - > E; ~3.68 (m): 2H (H$_3$, H$_5$); 3.79 (bs) 1H - - - > H$_{11}$; 4.24 (d): H'$_1$; 5.15 (dd): H$_{13}$; 3.29 (s) and 4.52 the OH's.

Use 1

2'-O-acetyl 3-O-de(2,6-dideoxy 3-C-methyl 3-O-methyl alpha-L-ribo-hexopyranosyl) 6-O-methyl erythromycin Stage A:

3-O-de(2,6-dideoxy 3-C-methyl 3-O-methyl alpha-ribo-hexopyranosyl) 6-O-methyl erythromycin A mixture of 513 mg of the product of Example 1, 5 ml of EtOH/water 1/1, 425 mg of sodium bisulphite and 115 μl of formic acid is agitated under reflux for half an hour. After cooling the mixture down to ambient temperature, 5 ml of a saturated solution of NaHCO$_3$ is added. The mixture is agitated for 5 minutes then extraction is carried out twice with AcOEt. The extraction phases are washed with 5 ml of a saturated solution of NaCl. The organic phase is dried over Na$_2$SO$_4$ and the solvent is evaporated off under vacuum. 180 mg of desired product is obtained, after chromatography on silica with AcOEt 95/MeOH 3/TEA 2 as eluant. Yield: 48%.

Analytical results:

NMR (CDCl$_3$, 250 MHz)

Spectrum identical to the data in the literature 5.17 (d): H$_{13}$; 4.38 (d): H'$_1$; 3.93 (bs): mobile H; 3.85 (s): H$_{11}$; 3.68 (s): H$_5$; 3.54 to 3.62 (m): H$_3$, H'$_5$: 3.24 (m): H'$_2$; 2.98 (s): OMe; 2.25 (s): N(Me)$_2$; 1.37-1.31-1.27-1.25-1.21-1.18-1.14-1.11: the C$\underline{H}_3$-CH's; 0.83 (t): C$\underline{H}_3$-CH$_2$.

Stage B:

2'-O-acetyl 3-O-de(2,6-dideoxy 3-C-methyl 3-O-methyl alpha-L-ribo-hexopyranosyl) 6-O-methyl erythromycin The product of the preceding stage is subjected to the action of acetic anhydride and the desired product is obtained.

Use 2:

2'-O-acetyl 3-O-de(2,6-dideoxy 3-C-methyl 3-O-methyl alpha-L-ribo-hexopyranosyl) 6-O-methyl erythromycin Stage A:

9-O-(2-methoxy 2-methylethyl) oxime of 3-O-de(2, 6-dideoxy 3-C-methyl 3-O-methyl alpha-L-ribo-hexopyranosyl) 6-O-methyl erythromycin 8.25 ml of 1M tetrabutyl ammonium fluoride in tetrahydrofuran is added rapidly at ambient temperature to a mixture of 2.75 g of the product of Example 1 and 5.5 ml of tetrahydrofuran, then agitation is carried out for 45 minutes. Next a mixture of 15 ml of ethyl acetate and 15 ml of ice-cooled water are added. After decanting, the organic phase is reextracted with 3 ml of water. 0.82 ml of concentrated ammonium hydroxide is added to the aqueous phase. The aqueous phase is extracted with ethyl acetate. The organic phase is washed with 3 ml of a solution of water saturated with sodium chloride then it is dried over sodium sulphate and the solvent is evaporated off under reduced pressure. 2.17 g of desired product is recovered. Yield: 95.7%

Analytical results:

NMR (CDCl$_3$, 300 MHz)

0.84 (t): C$\underline{H}_3$-CH$_2$; 0.97 (d)-1.10 (d)-1.18 (d)-1.24 (d)-1.26 (d) the C$\underline{H}_3$-CH's; 1.20–1.40 (x 2)-1.48 the C$\underline{H}_3$-C's; 2.26 (s): N(Me)$_2$; 2.13 (bq): H$_4$; 2.48 (m): H'$_3$; ~2.66: H$_{10}$ and H$_2$; 2.98 (s): OMe in position 6; 3.22 (s): OMe chain; ~3.26: H'$_2$; ~3.54: H$_3$ and H'$_5$; 3.68 (s)-3.83 (d): H$_5$ and H$_{11}$; ~3.73 (m) H$_8$ - - - > E; 4.38 (d): H'$_1$; 5.23 (dd): H$_{13}$.

Stage B:

9-O-(2-methoxy 2-methylethyl) oxime of 2'-O-acetyl 3-O-de(2,6-dideoxy 3-C-methyl 3-O-methyl alpha-ribo-L-hexopyranosyl) 6-O-methyl erythromycin A mixture of 2.17 g of the product prepared in the preceding stage, 22 ml of CH$_2$Cl$_2$ and 390 μl of acetic anhydride is agitated for one hour 30 minutes at ambient temperature. 22 ml of a saturated solution of sodium bicarbonate is added. The organic phase is washed with 10 ml of salt water. The aqueous phases are reextracted with CH$_2$Cl$_2$. The organic phase is dried over sodium sulphate, then the solvent is evaporated off under reduced pressure. The residue obtained is taken up in 4.25 ml of isopropyl ether then 14.9 ml of heptane. After agitation for 5 minutes, the precipitate is separated off then washed with heptane. After drying 1.72 g of desired product (colourless crystals) is recovered, M.p.=200° C. Yield: 74.7%.

Analytical results:

NMR (CDCl$_3$, 300 MHz)

0.83 (t): C<u>H</u>$_3$-CH$_2$; 0.92 (d)-0.97 (d)-1.17 (d)-1.28 (d)-1.30 (d) the C<u>H</u>$_3$-CH's; 1.18-1.29-1.40-1.47 the C<u>H</u>$_3$-C's; 2.06 (s): OAc; 2.26 (s): N(Me)$_2$; 2.59 (bq): H$_{10}$; 2.69 (m): H'$_3$ and H$_2$; 2.95 (s): OMe in position 6; 3.22 (s): OMe chain; ~3.47: H$_3$; H$_8$ and H'$_5$; 3.73 (d): H$_5$ and 3.79 (bs): H$_{11}$; 4.60 (d): H'$_1$; 4.77 (dd): H'$_2$; 5.23 (dd): H$_{13}$; 1.72 (d)-3.32- 4.63: mobile H's.

Stage C:

2'-O-acetyl 3-O-de(2,6-dideoxy 3-C-methyl 3-O-methyl alpha-L-ribo-hexopyranosyl) 6-O-methyl erythromycin A mixture of 180 mg of the product prepared in the preceding stage, 1.8 ml of ethanol/water 1/1, 23 μl of 98% formic acid and 180 mg of sodium bisulphite is agitated under reflux for 3 hours 30 minutes. The mixture is cooled down to ambient temperature and 1.8 ml of a saturated solution of sodium bicarbonate is added. After agitation for 3 minutes, extraction is carried out twice with CH$_2$Cl$_2$. The organic phase is washed with 2 ml of a saturated aqueous solution of NaCl. The organic phase is dried over sodium sulphate and the solvent is evaporated off under reduced pressure. After purification of the residue by chromatography on silica, eluting with ethyl acetate with 2% tetrahydrofuran, 43 mg of desired product is recovered. Yield: 27%.

Analytical results:

IR:

| -OH | ~3626 cm$^{-1}$ (Max) |
| | 3500 cm$^{-1}$ |
| >=O | 1735 cm$^{-1}$ |
| | 1689 cm$^{-1}$. |

We claim:

1. The compounds of formula (I):

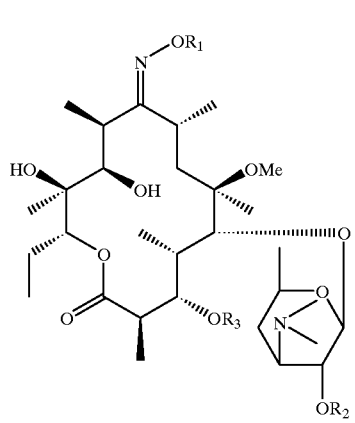

in which:

either R$_1$ represents an alkyl radical containing up to 8 carbon atoms substituted by one or more alkyl radicals containing up to 8 carbon atoms, or by one or more aryl radicals containing up to 14 carbon atoms, or R$_1$ represents an aryl radical containing up to 14 carbon atoms, optionally substituted by one or more alkyl, alkenyl or alkynyl radicals containing up to 8 carbon atoms, alkoxy or alkylthio radicals containing up to 8 carbon atoms, nitro, CF$_3$ radicals or by one or more halogen atoms, or R$_1$ represents a radical:

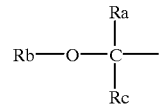

in which Ra represents an alkyl or alkoxy radical containing up to 8 carbon atoms, Rb represents an alkyl radical containing up to 8 carbon atoms, optionally substituted by a heteroatom, Rc represents a hydrogen atom or an alkyl radical containing up to 8 carbon atoms, R$_2$ and R$_3$, identical or different, represent a trialkyl-silyl radical in which the alkyl radical contains up to 8 carbon atoms,

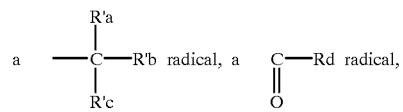

in which R'a, R'b, R'c and Rd represent an alkyl radical containing up to 8 carbon atoms, or an aralkyl radical containing up to 8 carbon atoms, optionally substituted by one or or more of the substituents indicated above for R$_1$.

2. The compounds of formula (I) as defined in claim 1 in which R$_1$ represents a

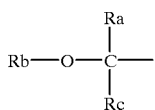

radical in which Ra, Rb and Rc retain the same meaning as in claim 1.

3. The compounds of formula (I) as defined in claim 2, in which Ra, Rb and Rc represent a methyl radical.

4. The compounds of formula (I) as defined in claim 1, in which $R_2$ and $R_3$ both represent a trialkylsilyl radical.

5. The compounds of formula (I) as defined in claim 4, in which $R_2$ and $R_3$ represent a trimethylsilyl radical.

6. The compound of formula (I) defined in claim 1 whose name follows:

9-O-(2-methoxy-2-methylethyl) oxime of 3-O-de(2,6-dideoxy-3-C-methyl-3-O-methyl-alpha-L-ribo-hexopyranosyl)-2'O,3-O-bis-(trimethylsilyl)-6-O-methyl erythromycin.

7. Preparation process for the compounds of formula (I) as defined in any claim 1, characterized in that the compound of formula (II):

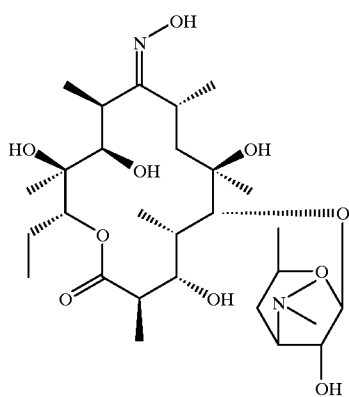

is subjected to the action of an agent blocking the oxime in position 9, in order to obtain a compound of formula (III):

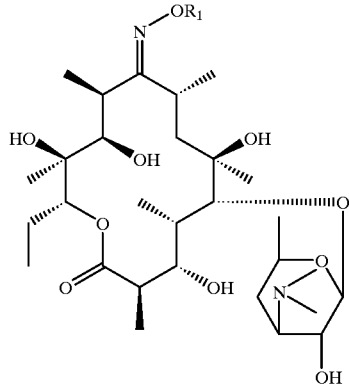

in which $R_1$ retains its previous meaning, which is subjected to the action of an agent blocking the hydroxyl in position 3 and in position 2' in order to obtain the compound of formula (IV):

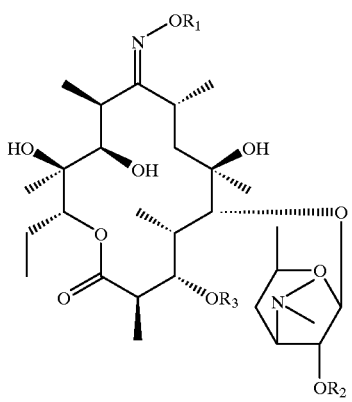

in which $R_1$, $R_2$ and $R_3$ retain their previous meaning, which is subjected to the action of a methylation agent of the hydroxyl in position 6, in order to obtain the corresponding compound of formula (I).

8. Preparation process according to claim 7, characterized in that the methylation of the compound of formula (IV) is carried out using methyl iodide in the presence of a base.

9. As new chemical products, the compounds of formulae (III) and (IV) as defined in claim 7.

10. As chemical products defined in claim 9, the following products:

9-O-(2-methoxy-2-methylethyl) oxime of 3-O-de(2,6-dideoxy-3-C-methyl-3-O-methyl-alpha-L-ribo-hexopyranosyl) erythromycin, 9-O-(2-methoxy-2-methylethyl) oxime of 3-O-de(2,6-dideoxy-3-C-methyl-3-O-methyl-alpha-L-ribo-hexopyranosyl)-2'O,3-O-bis(trimethylsilyl) erythromycin.

11. A process comprising reacting a compound of claim 1 with formic acid in the presence of sodium bisulphite or sodium metabisulphite, to obtain the compound of the formula

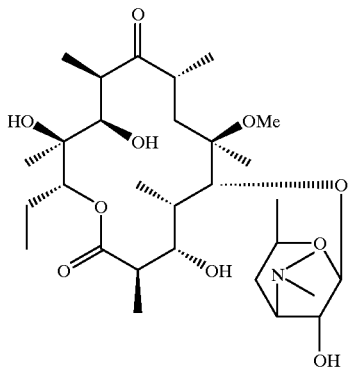

reacting the latter with a protection agent of the hydroxyl in position 2' to obtain the compound of the formula (VI)

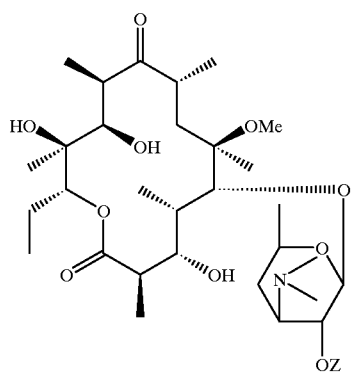

in which Z is selected from the group consisting of an acyl of a carboxylic acid of up to 8 carbon atoms, trialkylsilyl, terbutyl and triphenylmethyl.

12. A process comprising reacting a compound of claim 1 with an agent releasing the hydroxyl in position 3 and in position 2' to obtain the compound of formula (VII)

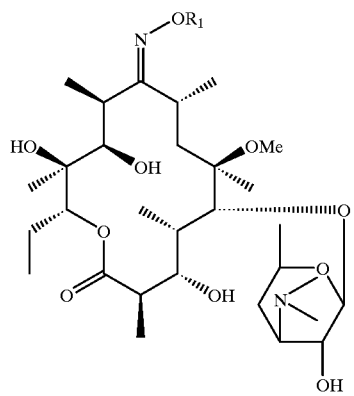

in which $R_1$ retains its previous meaning, reacting the latter with a protection agent of the OH group in position 2' to obtain the compound of formula (VIII)

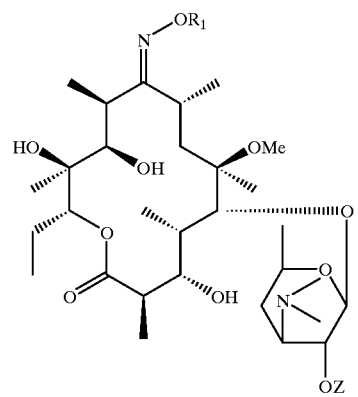

in which $R_1$ retains its previous meaning and Z represents a protective group as defined previously, and reacting the latter with an agent releasing the 9-oxo group in order to obtain the corresponding compound of the formula (VI)

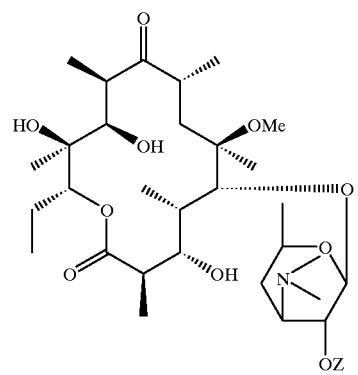

which Z retains its previous meaning.

13. A process comprising reacting a compound of claim 1 to release the oxime in position 9, reacting the resulting compound to release the 3 and 2' hydroxyl groups and protecting the 2'-hydroxyl.

* * * * *